United States Patent [19]

Kambanis et al.

[11] 4,166,893
[45] Sep. 4, 1979

[54] HYDROXY UNSATURATED DIESTERS AND COPOLYMERS THEREOF

[75] Inventors: Stamatis M. Kambanis; Alan D. Roberts; Walter Schank, all of Downsview, Canada

[73] Assignee: Reichhold Chemicals Limited, Islington, Canada

[21] Appl. No.: 838,863

[22] Filed: Oct. 3, 1977

Related U.S. Application Data

[63] Continuation-in-part of Ser. No. 630,904, Nov. 11, 1975, abandoned.

[30] Foreign Application Priority Data

Nov. 26, 1974 [CA] Canada .................................. 214705

[51] Int. Cl.² ..................... C08F 218/14; C08F 218/16
[52] U.S. Cl. ................................. 526/75; 204/159.22; 526/317; 526/320; 560/199
[58] Field of Search ................................. 526/75, 320

[56] References Cited

U.S. PATENT DOCUMENTS

| | | | |
|---|---|---|---|
| 3,406,221 | 10/1968 | Wright et al. | 526/320 |
| 3,969,328 | 7/1976 | Kurz | 526/320 |

FOREIGN PATENT DOCUMENTS 507192  6/1971  Switzerland .

*Primary Examiner*—Harry Wong, Jr.
*Attorney, Agent, or Firm*—Larson, Taylor and Hinds

[57] ABSTRACT

Process for the production of monomeric monohydroxy unsaturated diesters of formula I

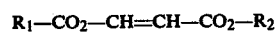

wherein: $R_1$ represents an alkyl group of two to six carbon atoms containing a free hydroxyl group, or 2,3-dihydroxy-propyl group, or a group of formula $+(CH_2)_nO+_m[(CH_2)_x+OH$ wherein n is 2 or 3, x is 2 or 3, and m is 1 to 800; $R_2$ represents an alkyl group of linear or branched configuration containing 4 to 12 carbon atoms. These compounds may be copolymerized in solution or suspension by free radical processes with an alkylacrylate and a third olefinically unsaturated monomer. These copolymers can be crosslinked with amino resins to provide thermosetting film-forming compositions.

12 Claims, No Drawings

HYDROXY UNSATURATED DIESTERS AND COPOLYMERS THEREOF

RELATED APPLICATION

This application is a continuation-in-part of applicant's copending application Ser. No. 630,904, filed Nov. 11, 1975, and now abandoned.

BACKGROUND OF THE INVENTION

Maleic anhydride, maleic acid, fumaric acid, and itaconic acid are used on a commercial scale for the synthesis of (a) unsaturated polyesters and (b) monoesters and diesters with monobasic fatty alcohols.

Group (a) products can be synthesized so that they contain terminal hydroxy groups. Such hydroxy terminated unsaturated polyesters are capable of polymerizing with acrylic and vinyl monomers, and of reacting with amino resins. Their reaction with amino resins leads to crosslinking under the influence of heat. Therefore, such polyesters can form thermosetting compositions. On the other hand, the group (a) polyesters are polymeric with regard to their unsaturation (that is, many double bonds per molecule) and, therefore, their copolymerization with other monomers, such as acrylic esters, and vinyl acetate, leads to rapid crosslinking and gellation.

Consequently, copolymerization of polymeric unsaturated polyesters with other unsaturated monomers, such as acrylic and methacrylic esters, and vinyl acetate, cannot apparently yield commercially useful solution or emulsion copolymers.

Group (b) monoesters and diesters are used as comonomers in solution, and in emulsion copolymers. However, they cannot impart hydroxyfunctionality and therefore crosslink ability, to any of their copolymers.

The compounds produced by the process of this invention are a variant of the group (b) diesters. The produced compounds are diesters prepared from an ethylenically unsaturated acid, typically maleic acid or anhydride, a primary alcohol, and a polyol. They therefore contain at least one reactive hydroxyl group in addition to the ethylenic bond.

Attempts have been made hitherto to prepare these compounds, since they should exhibit properties making them useful in copolymer systems with acrylic and other olefinically unsaturated monomers. None of these methods have proved to be commercially viable.

The most studied route is essentially a two step sequence. In a first step, a monoester, sometimes referred to as a half ester, of the ethylenically unsaturated diacid is prepared. This monoester is then reacted with an alkylene oxide, usually ethylene oxide or propylene oxide, (see U.S. Pat. Nos. 3,270,088; 3,399,229; 3,360,544; 3,481,973 and 3,494,605). This procedure has been found by us to have certain disadvantages. The first one is that it is limited to producing compounds where the hydroxyl group is beta to the ester linkage: this follows as a direct consequence of the opening of the 3-member oxide ring. This process is also not amenable to producing compounds containing more than one hydroxyl group. But what is perhaps most important these processes require as catalysts quite powerful compounds (e.g. U.S. Pat. Nos. 3,399,229 uses chromium trichloride; 3,481,973 uses pyridine, lutidine and other strong bases; 3,270,088 uses triethylamine) which cannot be readily removed from the product, as is some times admitted, for example the statement that the "product is only weakly green colored" in U.S. Pat. No. 3,399,229. It is our belief that the presence of these catalyst residues has an extremely adverse effect on the reaction products obtained. We have failed to prepare adequate copolymer systems from such products.

The attraction of the alkylene oxide route is that not until the oxide ring is opened is there a full hydroxyl group: therefore this method should minimize polyester formation. An alternative approach to this avoidance of polyester formation which has been described is to use dilute reaction systems (see U.S. Pat. No. 3,418,363). This process has two commercial disadvantages. First, the isolation of the required ester is complex. Second, unless considerable amounts of alcohol, polyol, and monoester are recycled to the system, the yield of diester produced is small when based on the amounts of alcohol and polyol taken: U.S. Pat. No. 3,418,363 recommends molar ratios of 2 to 10 moles each of alcohol and polyol per mole of dibasic acid.

We have now found that provided a particular catalyst is used, and provided that particular molar ratios of alcohol, polyol, and dibasic acid are used, then hydroxyl group containing unsaturated diesters can be prepared in a largely monomeric state by a simple process. The monomeric nature of the product has been established in two separate ways. First, by instrumental analysis techniques, particularly NMR. Second, by successful copolymer preparation both in solution and in an aqueous emulsion.

SUMMARY OF THE INVENTION

The present invention relates to a process for the synthesis of hydroxy group containing unsaturated diesters in monomeric form which overcome many of these disadvantages. Thus this invention provides diesters containing both at least one free hydroxyl group and an ethylenic double bond which are capable of being copolymerised with other monomers.

Thus this invention provides a process for the preparation of monohydroxy unsaturated diesters of formula I

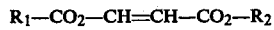

$$R_1-CO_2-CH=CH-CO_2-R_2 \qquad I$$

wherein $R_1$ represents an alkyl group of two to six carbon atoms containing one free hydroxyl group; or 2,3-dihydroxy propyl group, or a group of formula II

$$+(CH_2)_nO_{m}+(CH_2)_x+OH \qquad II$$

wherein n=2 or 3, x=2 or 3 and m is from 1 to 800; and $R_2$ represents an alkyl group of linear, or branched configuration containing four to twelve carbon atoms; which comprises reacting together a polyol of formula $R_1OH$, an alcohol of formula $R_2OH$ with an acid of formula $HO_2C-CH=CH-CO_2H$ or with an anhydride of such acid, wherein $R_1$ and $R_2$ are as defined above in the presence of paratoluene sulphonic acid as esterification catalyst in the proportions of 1 mole of polyol of formula $R_1OH$, to 1.1 moles of primary alcohol of formula $R_2OH$, to 1 mole of acid of formula $HO_2C-CH=CH-CO_2H$ or anhydride thereof, and isolating the monomeric unsaturated diester so produced.

Preferably any remaining excess alcohol is removed from the product after esterification has been carried out, conveniently by distillation.

Preferred combinations of polyol $R_1OH$, primary alcohol $R_2OH$ and acid $HO_2C-CH=CH-CO_2H$ are:

(i) isobutanol, ethylene glycol, and maleic acid or anhydride;
(ii) butanol, ethylene glycol, and maleic acid or anhydride;
(iii) 2-ethylhexanol, ethylene glycol, and maleic acid or anhydride;
(iv) isobutanol, 1,2-propylene glycol, and maleic acid or anhydride;
(v) isobutanol, glycerol, and maleic acid or anhydride;
(vi) isobutanol, ethylene glycol, and fumaric acid.

In an alternative aspect this invention provides a copolymer capable of crosslinking to provide a thermosetting system wherein the copolymer is derived from monomers of the following three classes in the percentage weight proportions given:

(a) from 11% to 30% of a diester of formula (I):

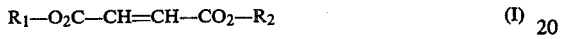
$$R_1-O_2C-CH=CH-CO_2-R_2 \qquad (I)$$

wherein $R_1$ and $R_2$ are as hereinbefore defined, and which has been prepared by the process hereinbefore described, (b) from 2% to 35% of an alkyl acrylate having up to eight carbon atoms in the alkyl group, which alkyl group may be of linear or branched configuration; and (c) remainder an olefinically unsaturated monomer of the styrene, vinyl, acrylic, or methacrylic classes.

Preferably the diester is chosen from a reaction product obtained from one of the following reactant combinations:

(i) isobutanol, ethylene glycol, and maleic acid or anhydride;
(ii) butanol, ethylene glycol, and maleic acid or anhydride;
(iii) 2-ethylhexanol, ethylene glycol, and maleic acid or anhydride;
(iv) isobutanol, 1,2-propylene glycol, and maleic acid or anhydride;
(v) isobutanol, glycerol, and maleic acid or anhydride;
(vi) isobutanol, ethylene glycol, and fumaric acid.

Preferably the alkyl acrylate is chosen from butyl acrylate, and 2-ethyl hexyl acrylate.

Conveniently the third olefinically unsaturated monomer is chosen from at least one of the group consisting of methyl methacrylate, acrylic acid, vinyl acetate, and styrene.

Such polymers are conveniently prepared by reacting the specified monomers, in solution or suspension, in the presence of a free-radical catalyst and at a temperature of from 50° C. to 100° C., preferably 65° C. to 75° C.

Preferably isopropanol is used as the solvent for solution polymerization. For suspension polymerization, water containing sufficient surfactant to provide a stable aqueous emulsion is preferred.

DETAILED DESCRIPTION OF THE INVENTION

The subject unsaturated diesters containing reactive hydroxyl groups are copolymerizable with both acrylic and methacrylic ester monomers and vinyl acetate to give solution and emulsion polymers with commercially acceptable physical properties (low viscosity, film formers).

Furthermore, these polymers can be crosslinked with amino resins to give thermosetting protective coatings.

The subject compounds possess a chemical structure with unique chemical properties, namely, they can yield acrylic and polyvinyl acetate solution and emulsion copolymers with thermosetting capabilities.

The general synthesis of the subject compounds is based on the following procedure. This procedure has been found, quite unexpectedly to provide diesters both in good yield, and with only a low polyester content.

One mole of unsaturated acid or anhydride is reacted with one mole of a polyol and with 1.1 mole of primary alkanol at 150°–170° C. in the presence of paratoluenesulfonic acid (0.2% on total loaded reactants). The water of esterification is continuously removed from the distillate by decantation while the fatty alcohol is continuously returned to the reacting mixture. The following diols and triols were used for the subject synthesis:
Ethylene glycol
1,2-Propylene glycol
Diethylene glycol (i.e. $HOCH_2CH_2OCH_2CH_2OH$)
Glycerol
Polypropylenoxydiol (Voranol (trademark) P1010)

In general all diols would give monomeric unsaturated diesters with pending hydroxy groups.

Instrumental (GLC, IR, NMR) and wet techniques were used to determine the predominant chemical structure of the subject compounds. The analytical results confirmed the predominately monomeric (one double bond per molecule) structure, given herein.

The subject compounds were solution copolymerized with acrylate esters, methacrylate esters, styrene and vinyl acetate in propanol and in butyl cellosolve in the presence of butyl peroctoate or benzoyl peroxide at 92°–97° C.

The resulting copolymers contained 70–75% polymer at viscosities of 9000–20000 cps. These copolymers were crosslinkable and thermosetting in the presence of amino resins.

The subject compounds were emulsion copolymerized with vinyl acetate, styrene, acrylate and methacrylate esters in an aqueous phase containing surface-active agents at 60°–75° C. The resulting emulsion copolymers contained 44–55% polymer at viscosities of 500–2000 cps.

These emulsion copolymers were crosslinkable and thermosetting in the presence of amino resins.

The following examples set forth specific embodiments of the instant invention. However, the invention is not to be construed as being limited to these embodiments for there are, of course, numerous possible variations and modifications. All parts and percentages in the examples as well as throughout the specification are by weight.

EXAMPLE 1

A round bottom cylindrical reactor vessel equipped with fractionating column, condenser, fatty alcohol - water separator/decanter, stirrer, thermometer and a heating means was charged with the following materials:

| | | |
|---|---|---|
| Maleic anhydride | 588 g. | 6.0 moles |
| Isobutanol | 590 g. | 6.6 moles |
| Ethylene glycol | 372 g. | 6.0 moles |
| Paratoluenesulfonic acid | 3 g. | — |

| | | |
|---|---|---|
| Water | 5 g. | — |

The reactants were heated to 105° C. A strong exotherm brought the reaction temperature to 120° C. within 30 minutes. As soon as the exotherm ran its course, the temperature was increased to 135°–140° C. Most of the esterification reaction took place at 140° C. During this period 75 g. of water were collected. Then the temperature increased to 165°–170° C. During this period an additional 21 g. of water were collected. Then, 45 g. of isobutanol were distilled off. During this last period the Acid Number dropped to 8.

The analysis of the resulting product gave the following results:

| | |
|---|---|
| Acid number | 8 |
| Hydroxyl Number | 230 |
| Viscosity | 120 cps. |
| 2-Hydroxyethyl Butyl Ester Content | 82% |
| Other Ester Species | 15% |
| Free Isobutanol | 3% |

EXAMPLE 2

This was identical to Example 1 in all respects except for replacing isobutanol with n-butanol.

The analysis of the resulting product gave the following results:

| | |
|---|---|
| Acid Number | 8 |
| Hydroxyl Number | 230 |
| Viscosity | 120 cps. |
| 2-Hydroxyethyl Butyl Ester Content | 82% |
| Other Ester Species | 15% |
| Free n-butanol | 3% |

EXAMPLE 3

Equipment and reaction conditions were identical to those of Example 1. However, the reactor was loaded with the following materials:

| | | |
|---|---|---|
| Maleic anhydride | 490 g. | 5.0 moles |
| Octanol* | 715 g. | 5.5 moles |
| Ethylene glycol | 310 g. | 5.0 moles |
| Paratoluenesulfonic acid | 3 g. | — |
| Water | 5 g. | — |
| Esterification water collected = | 85 g. | |
| Octanol* distilled off = | 57 g. | |
| Analysis: | | |
| Acid number | 10 | |
| Hydroxyl number | 185 | |
| Viscosity | 120 cps. | |
| 2-Hydroxyethyl octyl ester content | 85% | |
| Other ester species | 10% | |
| Free octanol | 5% | |

*The octanol used is 2-ethylhexanol.

EXAMPLE 4

Equipment and reaction conditions were identical to those of Example 1. However, the reactor was loaded with the following materials:

| | | |
|---|---|---|
| Maleic anhydride | 588 g. | 6.0 moles |
| Propylene glycol | 456 g. | 6.0 moles |
| Isobutanol | 490 g. | 6.6 moles |
| Paratoluenesulfonic acid | 3 g. | — |
| Water | 5 g. | — |
| Esterification water collected = | 96 g. | |
| Isobutanol distilled off = | 75 g. | |
| Analysis: | | |
| Acid number | 10 | |
| Hydroxyl number | 180 | |
| Viscosity | 110 cps. | |
| 2-Hydroxy-propyl butyl ester content | 81% | |
| Other ester species | 16% | |
| Isobutanol | 3% | |

EXAMPLE 5

Equipment and reaction conditions were identical to those of Example 1. However, the reactor was loaded with the following materials:

| | | |
|---|---|---|
| Maleic anhydride | 588 g. | 6.0 moles |
| Isobutanol | 490 g. | 6.6 moles |
| Diethylene glycol* | 636 g. | 6.0 moles |
| Paratoluenesulfonic acid | 3 g. | — |
| Water | 5 g. | — |
| Esterification water collected = | 94 g. | |
| Isobutanol distilled off = | 73 g. | |
| Analysis: | | |
| Acid number | 12 | |
| Hydroxyl number | 167 | |
| Viscosity | 160 cps. | |
| 2(-(2-hydroxyethoxy)ethyl butyl ester content | 80% | |
| Other ester species | 16% | |
| Free Isobutanol | 4% | |

*That is the compound of formula $HOCH_2CH_2OCH_2CH_2OH$.

EXAMPLE 6

Equipment and reaction conditions were identical to those of Example 1. However, the reactor was loaded with the following materials:

| | | |
|---|---|---|
| Maleic anhydride | 588 g. | 6.0 moles |
| Isobutanol | 490 g. | 6.6 moles |
| Glycerol | 522 g. | 6.0 moles |
| Paratoluenesulfonic acid | 3 g. | — |
| Water | 5 g. | — |
| Esterification water collected = | 90 g. | |
| Isobutanol distilled off = | 70 g. | |
| Analysis: | | |
| Acid number | 10 | |
| Hydroxyl number | 230 | |
| Viscosity | 600 cps. | |
| Di(hydroxy propyl) butyl ester content | 70% | |
| Other ester species | 27% | |
| Free isobutanol | 3% | |

EXAMPLE 7

Equipment and reaction conditions were identical to those of Example 1. However, the reactor was loaded with the following materials:

| | | |
|---|---|---|
| Maleic anhydride | 98 g. | 1.0 moles |
| Isobutanol | 82 g. | 1.1 moles |
| Polypropyleneoxydiol (Voranol P.1010) | 1000 g. | 1.0 moles |
| Paratoluenesulfonic acid | 2 g. | — |
| Water | 5 g. | |
| Esterification water collected = | 20g. | |
| Isobutanol distilled off = | 10g. | |

-continued

| Analysis: | |
|---|---|
| Acid number | 12 |
| Hydroxyl number | 64 |
| Viscosity | 900 cps. |
| Hydroxy (polypropyleneoxy) butyl ester content | 72% |
| Other ester species | 20% |
| Free Voranol P.1010 | 5% |
| Free Isobutanol | 3% |

EXAMPLE 8

Equipment and reaction conditions were identical to those of Example 1. The reactor was loaded with the following materials:

| Fumaric acid | 696 g. | 6.0 moles |
|---|---|---|
| Isobutanol | 490 g. | 6.6 moles |
| Ethylene glycol | 372 g. | 6.0 moles |
| Paratoluenesulfonic acid | 3 g. | — |
| Water | 5 g. | — |
| Esterification started taking place at temperature high than 130° C. | | |
| Water of esterification collected = | 200 g. | |
| Isobutanol distilled off = | 70 g. | |
| Analysis: | | |
| Acid number | 11 | |
| Hydroxyl number | 190 | |
| Viscosity | 130 cps. | |
| Hydroxy ethyl ester content | 84% | |
| Other ester species | 12% | |
| Free isobutanol | 4% | |

EXAMPLE 9

Equipment and reaction conditions were identical to those of Example 1. The reactor was loaded with the following materials:

| Itaconic acid | 650 g. | 5.0 moles |
|---|---|---|
| Isobutanol | 407 g. | 5.5 moles |
| Ethylene glycol | 310 g. | 5.0 moles |
| P.T.S.A. | 3 g. | — |
| Water | 5 g. | — |
| Toluene hydroquinone (5% in isobutanol) | 5 g. | — |

The esterification reaction was slower than of maleic anhydride.

| Esterification water collected | = 170 g. |
|---|---|
| Isobutanol | = 35 g. |

This product tends to homopolymerize when exposed to sunlight.

| Acid number | 15 |
|---|---|
| Hydroxyl number | 180 |
| Viscosity | 200 cps. |
| Hydroxy ethyl butyl ester content | 80% |
| Other ester species | 16% |
| Free isobutanol | 4% |

The following examples illustrate the solution copolymerization of the compounds outlined in Examples 1 through 9, with acrylic, methacrylic and styrene monomers.

EXAMPLE 10

A cylindrical reactor equipped with a condenser, stirrer, thermometer, two addition vessels and a heating means was charged with 825 g. propanol. The temperature was brought to 90° C. and a monomer blend and a catalyst solution were added to the reactor over a period of five (5) hours.

| Monomer Blend: | |
|---|---|
| Methyl methacrylate | 1000 g. |
| Acrylic Acid | 300 g. |
| Butyl acrylate | 800 g. |
| Intermediate of Example 1. | 700 g. |
| Catalyst Solution: | |
| Propanol | 90 g. |
| t-Butyl peroctoate | 13 g. |

Free radical copolymerization was maintained at 96° C. under propanol reflux. The finished product had the following properties:

| Liquid viscosity | = | 13,000 cps. |
|---|---|---|
| Polymer content | = | 70% |

The ester intermediate of Example 1 was found to be completely copolymerized.

| Thermosetting Composition: | |
|---|---|
| Polymer of Example 12 | 100 |
| Water reducible amino resin (60%) | 10 |
| Dimethylethanolamine | 3 |
| Water | 30 |

A 3 mil film obtained from the above composition and exposed to 350° F. for five (5) minutes showed the following properties:

| Pencil hardness | = | 2H |
|---|---|---|
| MEK extractibles | = | 12% on solids |

Test Methods: A. Pencil Hardness

In this test, the hardness of a cured paint film is related to the hardness of a graphite pencil. A series of standard pencils, ranging from 4B to 4H is supplied by Staedtler (Germany).

About ¼" of lead is "squared" by rubbing against fine abrasive paper (400 carbide). The pencil is held at normal writing angle (45°) and pushed forward against the film, using pressure short of breaking the lead. Any marks or scratches, visible at an oblique angle under strong light, indicate that the pencil is harder than the film. The hardness is expressed as the grade of next softer pencil.

Grades in increasing order of hardness are:

4B, 3B, 2B, B, HB, F, H, 2H, 3H, 4H. B. MEK Extractibles

The solubility of a PVA—acrylic or acrylic polymer in methyl ethyl ketone decreases as the degree of crosslinking of this polymer increases. Therefore, the extractibility of a polymer in MEK can be used as an inverse measure of the degree of crosslinking.

A 3 mil film of the polymer is deposited from suspension or solution on an aluminum foil. 3–5 of this film is submitted to Soxhlet extraction by MEK for 24 hours.

The insoluble part is dried and weighed. Thus, the MEK extractibles or insolubles are determined as percent by weight.

EXAMPLES 11–18

The procedure of Example 10 was repeated, with the sole change that the ester intermediate used was that from one of Examples 2 to 9. The results are given in Table I.

TABLE I
SOLUTION COPOLYMERS OF EXAMPLES 14-18

| Intermediate used from: | Example No. | Viscosity, cps. | Polymer Content % | Pencil Hardness | MEK Extractibles |
|---|---|---|---|---|---|
| Example 2 | 11 | 15,000 | 72 | 2H | 10 |
| 3 | 12 | 9,000 | 67 | H | 15 |
| 4 | 13 | 17,000 | 67 | 2H | 11 |
| 5 | 14 | 10,000 | 67 | H | 14 |
| 6 | 15 | 18,000 | 67 | 3H | 8 |
| 7 | 16 | 10,000 | 68 | H | 14 |
| 8 | 17 | 13,000 | 70 | 2H | 12 |

Thus the solution polymers obtained from Examples 11–18 gave copolymers with the following property ranges:

| | |
|---|---|
| Liquids viscosity range | = 9,000–18,000 cps. |
| Polymer content (N.V.) | = 67–72% |
| Film properties of thermosetting compositions (Example 10) | |
| Pencil hardness | = H–3H |
| MEK extractibles | = 8–15% on solids |

The above examples show that the invented compounds give solution copolymers with thermosetting properties.

EXAMPLE 19

Equipment and reaction conditions were identical to those of Example 10. The monomer blend was made up of the following materials. The remaining materials were not changed:

| | |
|---|---|
| Styrene | 1000 |
| Butyl acrylate | 800 |
| Acrylic acid | 300 |
| Intermediate - Example 1. | 700 |
| Analysis: | |
| Viscosity | = 17,000 cps. |
| Polymer content | = 68% |
| Film properties of the thermosetting composition of Example 19. | |
| Pencil hardness | = 3H |
| MEK extractibles | = 13% |

This copolymer is also thermosetting.

The following examples illustrate the emulsion copolymerization of some of the compounds outlined in the Examples 1 to 9, with acrylic, methacrylic, styrene and vinyl acetate monomers.

EXAMPLE 20

A cylindrical reactor equipped with three addition vessels (for monomer, catalyst and activator), a condenser, stirrer and a thermometer was charged with the following materials:

| Aqueous Phase | |
|---|---|
| Water | 540 |
| Nonionic surfactants | 34 |
| Anionic surfactants | 26 |
| Protective colloid | 8 |

In the monomer addition vessel the following materials were blended:

| | |
|---|---|
| Vinyl acetate | 655 |
| Intermediate - Example 1 | 100 |
| 2-Ethylhexyl acrylate | 28 |

In the catalyst addition vessel the following materials were blended:

| | |
|---|---|
| Ammonium persulfate | 3 |
| Ammonia (26%) | 2.5 |
| Water | 27.5 |

In the activator addition vessel, the following materials were blended:

| | |
|---|---|
| Formopon (trademark) | 1 |
| Water | 32 |

The aqueous phase was heated to 72° C. and then 72 g. of the monomer blend were added to it. 1 g. of ammonium persulfate was added there and the emulsion polymerization was thus initiated. The exotherm raised the reaction temperature to 77° C. The monomer blend, catalyst solution and activator solution were added to the reactor over a period of six (6) hours. The resulting emulsion polymer showed the following properties:

| | |
|---|---|
| Polymer content (% N.V.) | = 55 |
| Viscosity (RVF #3/60 rpm) | = 1000 cps. |
| Free monomer | = 0.4% |
| Particle Size | = 0.2–0.4 microns |
| Film | = Continuous, clear. |

| Thermosetting Composition: | |
|---|---|
| Emulsion polymer - Example 20. | 100 g. |
| Water reducible UF resin | 10 g. |

A 3 mil film cast from the above blend was exposed to 350° F. for five (5) minutes. It was found to have the following properties:

| | |
|---|---|
| Pencil hardness | = H |

-continued

| | |
|---|---|
| MEK extractibles | = 15% |

From the above results, it is concluded that the emulsion polymer of Example 20 is crosslinkable in the presence of amino resins.

EXAMPLES 21–28

Equipment and reaction conditions were identical to those of Example 20, except that the intermediate from Example 1 was substituted by those of Example 2, 3, 4, 5, 6, 7, 8 and 9.

The results are given in Table II

TABLE II
EMULSION COPOLYMERS OF EXAMPLES 21–28

| Intermediate used from | Example No. | Viscosity cps. | Particle Size microns | Film | Pencil Hardness | MEK Extractibles % |
|---|---|---|---|---|---|---|
| Example 2 | 21 | 1,200 | 0.3–0.4 | ALL | H | 13 |
| 3 | 22 | 1,500 | 0.2–0.4 | | H | 17 |
| 4 | 23 | 1,500 | 0.3–0.5 | FILMS | 2H | 16 |
| 5 | 24 | 1,500 | 0.3–0.5 | | H | 17 |
| 6 | 25 | 1,500 | 0.3–0.5 | | 2H | 12 |
| 7 | 26 | 1,500 | 0.3–0.5 | WERE | H | 17 |
| 8 | 27 | 1,000 | 0.2–0.4 | | H | 12 |
| 9 | 28 | 1,500 | 0.2–0.4 | CLEAR | H | 15 |

Thus the emulsion polymer products obtained in Examples 21 to 28 had the following range of properties:

| | |
|---|---|
| Polymer content (% N.V.) | = 54–56 |
| Viscosity (#3/60 rpm) | = 1,000–1,500 cps. |
| Particle size | = 0.2–0.5 microns |
| Film | = Clear, continuous |

Crosslinkability:

The thermosetting composition of Example 20 gave films with the following properties:

| | | |
|---|---|---|
| Pencil hardness | = | H–2H |
| extractibles | = | 12–17% |

EXAMPLE 29

The ester intermediate of Example 1 was copolymerized with acrylic monomers, using identical equipment and conditions to those of Example 20, except for the following changes:

| Monomer Blend: | |
|---|---|
| Methyl methacrylate | 300 |
| Butyl acrylate | 240 |
| Acrylic acid | 50 |
| Intermediate of Example 1 | 100 |
| Aqueous Phase: | |
| Water | 540 g. |
| Nonionic surfactants | 18 g. |
| Anionic surfactants | 42 g. |

The reaction temperature was held at 68°–70° C. The resulting emulsion polymer showed the following properties:

| | |
|---|---|
| Polymer content (% N.V.) | = 47.5 |
| Viscosity | = 500 cps. |
| pH | = 7.5 |
| Particle Size | = 0.1–0.2 microns |
| Film | = Clear, continuous. |
| Free monomer | = 0.5%tz,1/32 |

Crosslinkability:

The thermosetting composition of Example 20 gave films with the following properties:

| | | |
|---|---|---|
| Pencil hardness | = | H |
| MEK extractibles | = | 20% |

EXAMPLE 30

Equipment and conditions were identical to those of Example 29 except that the methyl methacrylate was replaced by styrene, weight by weight. The resulting emulsion polymer showed the following properties:

| | |
|---|---|
| Polymer content (% N.V.) | = 47.6 |
| Viscosity | = 700 cps. |
| pH | = 7.5 |
| Particle Size | = 0.1–0.2 microns |
| Film | = Clear, continuous |
| Free Monomer | = 0.5% |

Crosslinkability:

With the thermosetting composition of Example 20.

| | | |
|---|---|---|
| Pencil hardness | = | H |
| MEK extractibles | = | 18% |

What we claim as our invention is:

1. A copolymer capable of cross linking to provide a thermosetting system, characterised in that the copolymer consists of monomers of the following three classes, in the weight percentages given:

(A) from 11% to 30% of an ester mixture consisting of at least 70% by weight of an unsaturated diester of formula (I)

$$R_1-O_2-CH=CH-CO_2-R_2 \qquad (I)$$

wherein:
$R_1$ represents (a) a monohydroxy alkyl group of two to six carbon atoms; or
(b) a 2,3-dihydroxypropyl group; or
(c) a group of the empirical formula (I)

$$\{-(CH_2)_nO\}_m\{-(CH_2)_x\}-OH \qquad (II)$$

in which formula n=2 or 3; x=2 or 3, and m is from 1 to 800; and $R_2$ represents a linear or branched primary alkyl group having from 4 to 12 carbon atoms;
which ester mixture has been prepared by reacting together 1.0 mole of a polyol of formula $R_1OH$, 1.1 moles of a primary alcohol of formula $R_2OH$ and 1 mole of an acid of formula $HO_2C-CH=CH-CO_2H$, or 1 mole of the anhydride thereof, in the presence of para-toluene sulphonic acid as catalyst;

(B) from 2% to 35% of an alkyl acrylate, having up to eight carbon atoms in the alkyl group, which group may be of linear or branched configuration; and (C) from 35% to 87% of at least one other monomer containing olefinic unsaturation, and chosen from the group consisting of methyl methacrylate, acrylic acid, vinyl acetate, and styrene.

2. Copolymer according to claim 1 characterised in that the unsaturated diester used is the reaction product of one of the following combinations of reactants:
(i) isobutanol, ethylene glycol, and maleic acid or anhydride;
(ii) butanol, ethylene glycol, and maleic acid or anhydride;
(iii) 2-ethylhexanol, ethylene glycol, and maleic acid or anhydride;
(iv) isobutanol, 1,2-propylene glycol, and maleic acid or anhydride;
(v) isobutanol, glycerol, and maleic acid or anhydride;
(vi) isobutanol, ethylene glycol, and fumaric acid.

3. Copolymer as claimed in claim 1 characterised in that the alkyl acrylate is chosen from butylacrylate or 2-ethylhexylacrylate.

4. Copolymer as defined in claim 1 characterised in that the olefinically unsaturated monomer (C) is selected from (i) methyl methacrylate together with acrylic acid; or (ii) vinyl acetate; or (iii) styrene together with acrylic acid.

5. Process for the preparation of a copolymer capable of cross linking to provide a thermosetting system, characterised in that monomers of the following three classes are reacted, in the weight percentages given, in solution or in suspension in the presence of a free radical catalyst and at a temperature of from 50° C. to 100° C., (A) from 11% to 30% of an ester mixture consisting of at least 70% by weight of an unsaturated diester of formula (I)

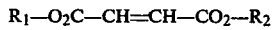   (I)

wherein
$R_1$ represents
(a) a monohydroxy alkyl group of two to six carbon atoms; or
(b) a group of the empirical formula (II)

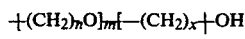   (II)

in which formula $n=2$ or 3; $x=2$ or 3, and $m$ is from 1 to 800; and $R_2$ represents a linear or branched primary alkyl group
having from 4 to 12 carbon atoms; which ester mixture has been prepared by reacting together 1.0 mole of a polyol of formula $R_1OH$, 1.1 moles of a primary alcohol of formula $R_2OH$ and 1 mole of an acid of formula $HO_2C-CH=CH-CO_2H$, or 1 mole of the anhydride thereof, in the presence of para-toluene sulphonic acid as catalyst;

(B) from 2% to 35% of an alkyl acrylate, having up to eight carbon atoms in the alkyl group, which group may be of linear or branched configuration; and (C) from 35% to 87% of at least one other monomer containing olefinic unsaturation, and chosen from the group consisting of methyl methacrylate, acrylic acid, vinyl acetate, and styrene, provided that the percentage amounts of (A), (B) and (C) always total to 100.

6. Process according to claim 5, characterised in that the reaction is carried out in isopropanol solution under reflux.

7. Process according to claim 5, characterised in that the reaction is carried out in water in the presence of sufficient surfactant to provide an aqueous emulsion.

8. Process according to claim 5, characterised in that the reaction is carried out at a temperature of from 65°–75° C.

9. Process according to claim 5, characterised in that the unsaturated diester used is the reaction product of one of the following combinations of reactants:
(i) isobutanol, ethylene glycol, and maleic acid or anhydride;
(ii) butanol, ethylene glycol, and maleic acid or anhydride;
(iii) 2-ethylhexanol, ethylene glycol, and maleic acid or anhydride;
(iv) isobutanol, 1,2-propylene glycol, and maleic acid or anhydride;
(v) isobutanol, glycerol, and maleic acid or anhydride;
(vi) isobutanol, ethylene glycol, and furmaric acid.

10. Process according to claim 5, characterised in that the alkyl acrylate is chosen from butylacrylate or 2-ethylhexylacrylate.

11. Process according to claim 5, characterised in that the olefinically unsaturated monomer (C) is selected from (i) methyl methacrylate together with acrylic acid; or (ii) vinyl acetate; or (iii) styrene together with acrylic acid.

12. Process according to claim 5, characterised in that the free radical catalyst is chosen from t-butyl peroctoate or ammonium persulphate.

* * * * *